US008801798B1

(12) United States Patent  (10) Patent No.: US 8,801,798 B1
Smith  (45) Date of Patent: Aug. 12, 2014

(54) BEARING FIXATION (71) Applicant: Biomet Manufacturing Corporation, Warsaw, IN (US)

(72) Inventor: Aaron P. Smith, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/763,145

(22) Filed: Feb. 8, 2013

(51) Int. Cl.
*A61F 2/32* (2006.01)
(52) U.S. Cl.
USPC ............. 623/22.24; 623/22.21; 623/22.25
(58) Field of Classification Search
CPC .......................................... A61F 2/34
USPC ................................. 623/22.17–22.39
See application file for complete search history.

(56) References Cited

U.S. PATENT DOCUMENTS

| 5,549,691 | A | 8/1996 | Harwin |
| 5,658,338 | A | 8/1997 | Tullos et al. |

FOREIGN PATENT DOCUMENTS

| DE | 4211346 A1 | 10/1993 |
| EP | 0500477 A1 | 8/1992 |

OTHER PUBLICATIONS

High Wall and Angled Liners, Research Disclosure database No. 587007, 2 pages (Mar. 2013).
Postak, et al., Performance Characteristics of Two Piece Acetabular Cups Series II, Orthopaedic Research Laboratories, 6 pages. (1996).
Rosca, et al., Enhanced Cross-Linked Polyethylene Modular Acetabular Designs: Performance Characteristics, Orthopaedic Research Laboratories, 4 pages (2008).
Tradonsky, et al., A Comparison of the Disassociation Strength of Modular Acetabular Components, Clinical Orthopaedics and Related Research, No. 296, pp. 154-160 (1993).
Invitation to Pay Additional Fees mailed Apr. 2, 2014 for partial search report of PCT/US2014/015057 (which claims priority to the present U.S. Appl. No. 13/763,145, filed Feb. 8, 2013).

*Primary Examiner* — Jason-Dennis Stewart
(74) *Attorney, Agent, or Firm* — Harness, Dickey (57) ABSTRACT

Disclosed is a bearing liner engageable within a shell member with an integrated projection portion. The integrated projection portion may deform a selected amount during positioning of the bearing liner within the shell. The shell may include a complementary engaging portion.

11 Claims, 5 Drawing Sheets

BEARING FIXATION

FIELD

The subject disclosure is related to fixing a deformable member to a second member, and particularly to fixing a liner to a shell.

BACKGROUND

This section provides background information related to the present disclosure, which is not necessarily prior art.

A subject can have a portion replaced with a replacement member. For example, a human patient subject can have a portion of the anatomy replaced with a prosthetic member. The reason for the replacement can be due to injury, disease, or other failing of the natural anatomy.

A prosthetic member can be used to replace a portion of the anatomy to substantially recreate or mimic the natural anatomy and physiology. For example, an acetabular prosthesis can be positioned in a prepared acetabulum of a patient to achieve a substantially natural or selected interaction of a femur and an acetabulum. It is understood in a complete or total hip arthroplasty that a proximal femoral portion may also be replaced.

An acetabular prosthesis can include a shell component that contacts a pelvis within an acetabulum. The shell can either interact with the natural femur or with a proximal femoral prosthesis directly, or a bearing can be placed in the shell. A bearing can be fixed in the shell using a separate element that is positioned between the bearing and the shell, such as with the RINGLOC® sold by Biomet, Inc.

SUMMARY

This section provides a general summary of the disclosure, and is not a comprehensive disclosure of its full scope or all of its features.

An acetabular prosthesis can be positioned in a patient to replace an acetabulum that is damaged or defective. The acetabular prosthesis can be placed in the patient after properly preparing the acetabulum to receive the acetabular prosthesis. The acetabular prosthesis can generally be formed of at least two pieces, including an external shell that is positioned in contact or cemented to the acetabulum of the pelvis and a bearing liner (also referred to herein alone as a liner or bearing) that is positioned and selectively fixed within the shell. Both the shell and the liner can include convex exterior surfaces and concave interior surfaces. The convex exterior surface of the shell can engage the bone of the pelvis and the convex exterior of the liner can engage the concave interior of the shell. The concave interior of the liner can then articulate relative to a proximal femur portion. The proximal femur can be a prosthetic member or natural proximal femur.

The liner can be engaged to the shell with an engagement portion defined by the liner. The engagement portion defined by the liner may engage and/or interact with the internal surface of the shell to selectively deform the liner during insertion of the liner into the shell. The engagement portion of the liner may then engage or be received by a depression formed within the shell. Once engaged with the depression the liner is substantially fixed to the shell for the purpose of the implantation.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
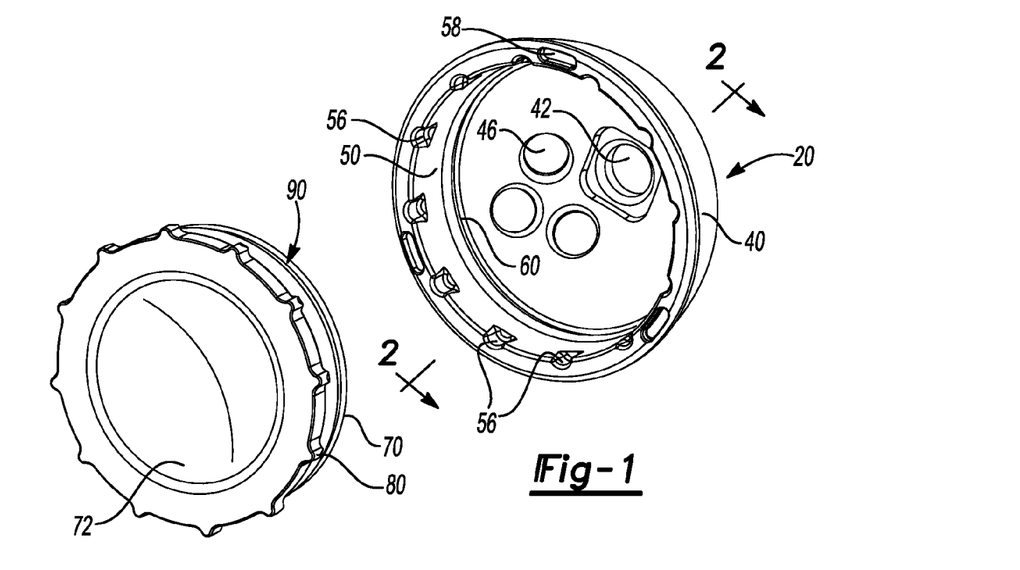
FIG. 1 is an exploded view of a shell and bearing liner, according to various embodiments.

With reference to FIG. 1, an acetabular prosthesis system can include a shell 20 and an acetabular liner 30. The shell 20 can include an exterior convex surface 40 that is configured to contact an acetabulum of a pelvis. The shell 20 can include throughbores, such as an apical throughbore defined by a sidewall 44 and one or more screw of fixation throughbores 46 defined by through sidewalls 48. The throughbores 46 extend from an interior concave surface 50 to the exterior convex surface 40. The apical hole 42 can generally be used for fixation and positioning of the acetabular shell 20 in the acetabulum. The fixation bore 46 can be used for passing a screw or other fixation member into the acetabular portion during implantation and fixation of the acetabular shell 20. It is understood that a plurality of the fixation throughbores 46 can be provided at various positions of the shell 20 and a user can selectively pass screws for fixing the shell 20 to the acetabulum of the subject. Additional mechanisms or features can be used to fix the shell to the pelvis as well, for example, projections or spikes, a porous coating or porous outer surface portion.

The acetabular shell 20 can also include other features, such as the anti-rotation depressions 56 formed near an upper surface or a rim 58 of the acetabular shell 20. The acetabular shell 20, including the anti-rotation depressions 56 can engage the liner 30 to hold the liner substantially rotationally fixed relative to the shell 20. Additionally, the shell 20 can include an interior groove or depression 60 formed as a substantially annular or circumferential depression within the concave surface 50 of the acetabular shell 20.

Figure 2:
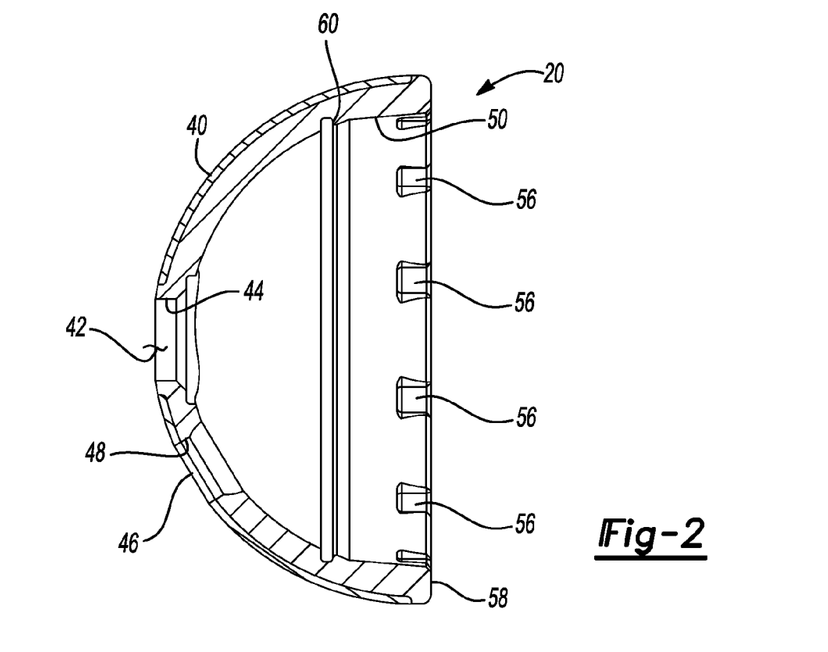
FIG. 2 is a cross-section view of the shell of FIG. 1.

The groove 60 formed within the shell 20 can be a groove formed within the shell similar to the groove formed in the shell of the acetabular shell used in the Ringloc® acetabular prosthesis sold by Biomet, Inc. having a place of business in Warsaw, Ind. The groove 60 formed in the interior surface 50 of the acetabular shell 20 can be formed with appropriate dimensions. The dimensions, as discussed further herein, can assist in fixation of the liner 30 relative to the shell 20 during and after an implantation of the liner 30 into the shell 20. Generally, the depression 60 substantially extends around the interior 50 of the shell 20 for fixing the liner 30 within the shell 20. It is understood, however, that alternative or additional fixation mechanisms can be provided or formed within the shell 20 to engage the liner 30.

Figure 3:
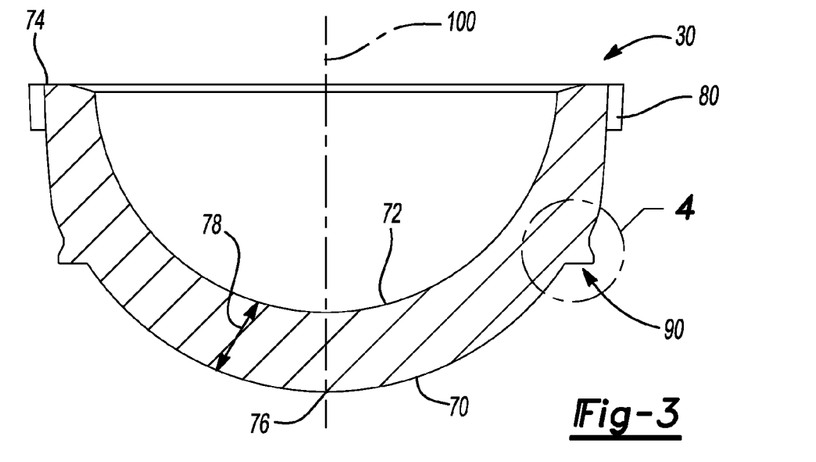
FIG. 3 is a cross-section view of the bearing liner of FIG. 1.

With continuing reference to FIG. 1, and additional reference to FIG. 3, the acetabular liner 30 can include an outer convex surface 70 and an inner concave surface 72. A liner rim 74 can be formed near an upper or equator region of the liner 30 positioned away from an apex 76 of the liner 30. A wall thickness between the interior concave surface 72 and the exterior convex surface 70 can be provided. It is understood that the wall thickness 78 can be substantially uniform or vary between the apex 76 and the rim 74 of the liner 30. The variation of the thickness of the wall of the liner 30 can be provided for various purposes such as insertion of the liner 30 within the shell 20 and other bearing characteristics, such as wear resistance or weight bearing.

Additionally, the liner 30 can be provided with a one or more anti-rotation projections 80 that extend from the outer surface 70 of the liner near the rim 74. The anti-rotation projections can engage the anti-rotation depressions 56 defined by the shell 20 for substantially rotationally fixing the liner 30 relative to the shell 20. Additionally, the anti-rotation projections 80 can assist in aligning the liner 30 relative to the shell 20. The anti-rotation projections can also assist in aligning the bearing 30 within the shell to ensure proper fixation therein.

Additionally, an axial fixation projection 90 can be formed to extend from the surface 70 of the liner 30. The axial fixation projection 90 can be formed as a substantially continuous projection around an exterior of the liner 30. Alternatively, the projection 90 can be formed as a segmental projection including discreet projection regions around the exterior of the liner 30. The axial fixation projection 90 may be formed to engage the axial fixation depression 60 within the shell 20 during an implantation and positioning of the liner 30 within the shell 20. As discussed herein, the geometry of the axial fixation projection 90 can interact with the inner surface 50 of the shell 20 during positioning of the liner 30 within the shell 20 and engage the depression 60 within the shell 20 for fixing the liner 30 within the shell 20.

Figure 4:
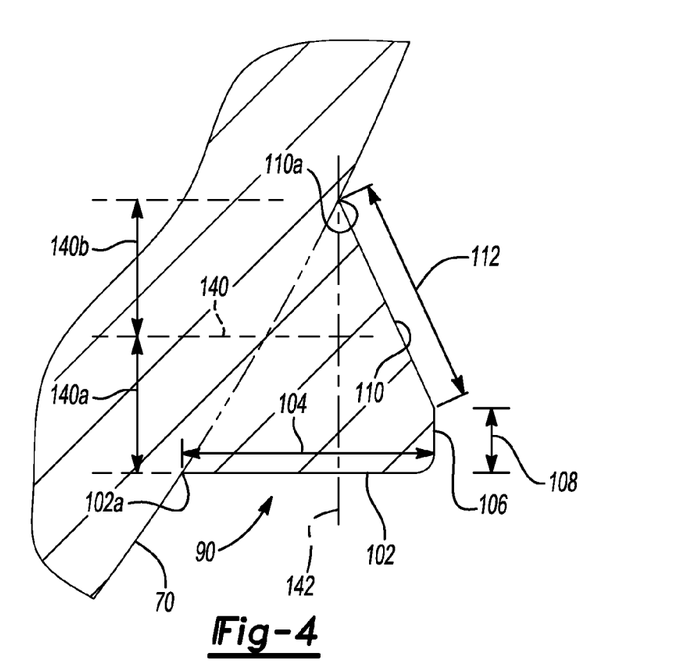
FIG. 4 is a detail cross-section view of an engagement portion taken from FIG. 3.

With continuing reference to FIG. 3 and additional reference to FIG. 4, the axial fixation projection 90 is shown in detail. The projection 90, illustrated in FIG. 4, is a manufactured or first configuration of the projection 90. As discussed herein, the projection can deform to engage and/or seat in the shell 20. The liner 30 can define a central axis 100 that extends substantially through the apex 76 of the liner 30. The central axis 100 is also generally perpendicular to a place defined near and/or by a rim of the liner 30. An apical or distal surface 102 of the axial fixation projection 90 can be formed to be substantially perpendicular or at a right angle to the axis 100 of the liner 30. The perpendicular surface 102 of the axial fixation projection 90 can extend a distance 104 from the exterior surface 70 of the liner 30. The distance 104 of the edge or surface 102 can provide, as discussed further herein, a sufficient or selected amount of material of the projection 90 to deform relative to the shell 20 for fixation within the depression 60 of the shell 20. The axial fixation projection 90 can further include a first parallel extending wall 106 that extends a parallel distance 108 of about 0.4 mm to about 0.6 mm, including about 0.5 mm. The parallel wall 108 extends substantially parallel to the central axis 100 of the liner 30. The parallel wall 106, however, can form an angle towards the central axis 100 from the perpendicular wall 102, such as about 68° relative to the perpendicular wall 102 of the axial fixation projection 90. A third angled wall 110 can extend from the parallel wall 106 to a juncture 111 along a distance 112. The distance 112 can be about 0.6 mm to about 0.8 mm, including about 0.7 mm. The angled wall 110 can extend at an angle towards the central axis 100 from the wall 106 at a generally acute angle towards the central axis 100 of the liner 30.

The exterior surface 70 generally defines an arc having a center defined relative to the liner 30. The exterior surface 70 is substantially continuous from the rim of the liner to an apex of the liner 30. The projection 90, including the various surfaces 102, 106, and 110 generally extends or diverges from the exterior surface 70 of the liner 30. Additionally, the measurements are exemplary regarding a liner generally having a diameter of about 31 mm. It is understood that the specific dimensions of the projection 90 can, therefore, differ based upon the dimensions of the liner 30.

According to various embodiments, the axial fixation projection 90 is formed of the same material as the remainder of the liner 30. Further, the projection 90 can be formed as one piece with the liner 30. For example, the liner 30 can be molded to include the projection 90 as an integral portion of the liner 30.

The projection 90 can be provided such that a majority of the material within the axial projection 90 is positioned below a midline 140 of the projection 90. The midline 140 is at the mid-point of the total axial distance of the projection 90. The total axial distance of the projection 90 can generally be defined as a distance between where the first surface 102 extends at 102a from the external surface 70 of the liner 30 to a point 110a where the surface 110 rejoins and/or extends from the external surface 70 of the liner 30. Accordingly, with reference to FIG. 4, the midline 140 of the projection 90 can be defined generally along line 140. Generally, the midline 140 is a first axial distance 140a from a line through the point 102a and a second axial distance 140b from a line through point 110a. The first axial distance 140a and the second axial distance 140b are equal when the line 140 is a true-mid-line. The lines through the points 102a and 110a are perpendicular to the central axis 100.

A vertical line or plane 142 is also defined relative to the liner 30. The vertical line 142 may be substantially parallel with the central axis 100 of the liner 30 and intersect the point 110a, where the wall 110 rejoins the outer surface 70. The mid-line 140 may be substantially perpendicular to the vertical line 142.

The mid-line 140 can define a boundary or a plane that divides material of the projection 90 between the rim and the apex of the liner 30. The vertical line 142 can define a central boundary of the projection 90. A majority, such as at least 51% of a volume of the material that defines the axial fixation projection 90 is between the mid-line 140 and the apex 76 of the liner 30 and the vertical line 142 and the outer edge of the projection 90. Thus, less than 51% of the volume of the material that defines the axial fixation projection 90 is between the line 140 and the upper rim 74 of the liner 30 and the vertical line 142 and the outer edge of the projection 90. According to various embodiments, however without being bound by the theory, providing a majority of the material in the axial fixation projection 90 closer to the apex 76 can allow for the projection 90 to deform as the liner 30 is moved into the shell 20. When the projection 90 deforms, the projection 90 can engage the depression 60 of the shell 20 after positioning the liner 30 within the shell 20 in a seated or changed configuration that is different from the original or manufactured configuration illustrated, for example, in FIG. 4.

Figure 5:
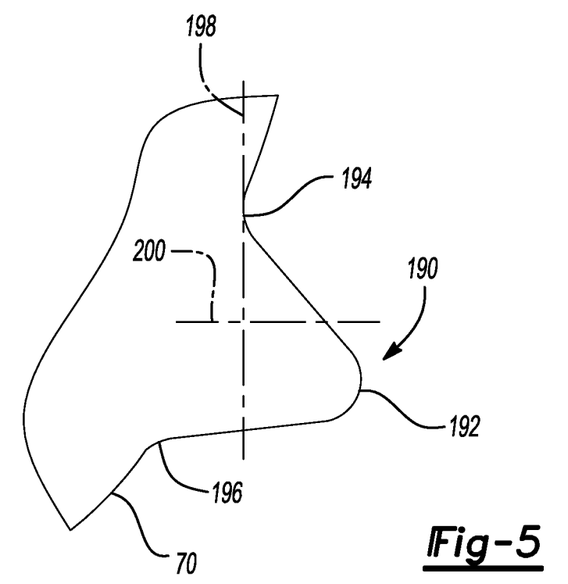
FIG. 5 is a detail cross-section view of an engagement portion, according to various embodiments.

According to various embodiments, as illustrated in FIG. 5, an alternative axial fixation projection 190 is illustrated. The liner 30 can include the exterior surface 70 and an axial fixation projection 190 that is substantially bulbous or curved. The projection 190 can include an exterior surface 192 that is substantially continuous from the first extension point 194 from the exterior surface 70 to the second diversion point 196, where the axial fixation projection 190 rejoins the exterior surface 70. A vertical line 198 extend substantially parallel to the central axis 100 of the liner and intersects the diversion point 194 (nearest the rim of the liner. The axial fixation projection 190 can include a majority of a volume of the material defined within the axial fixation projection 190 between a mid-line 200 and the apex 76 of the liner 30 and the vertical line 198 and an outer edge of the projection. Again, the mid-line 200 can be equidistant from lines that are perpendicular to the central axis 100 through the respective points 194 and 196.

Figure 6:
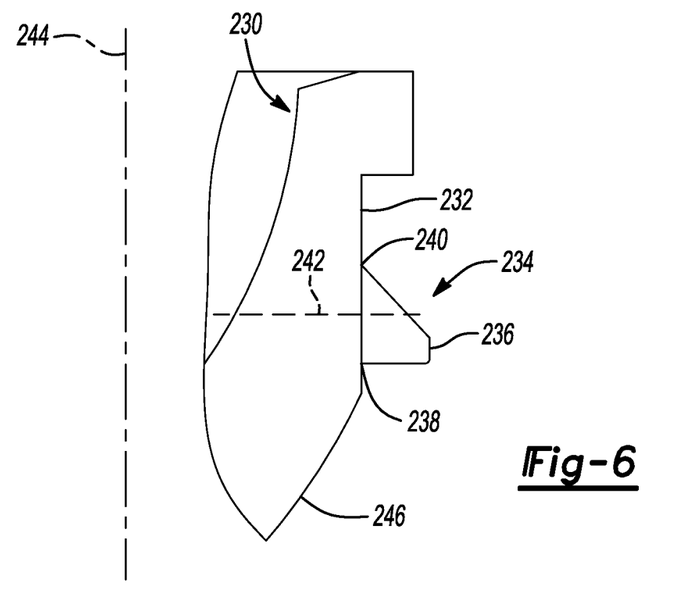
FIG. 6 is a detail cross-section view of an engagement portion, according to various embodiments.

According to various embodiments, with reference to FIG. 6, a liner 230 can be formed similar to the liner 30. The liner 230, however, can include a generally cylindrical outer surface region 232, such as near a rim of the liner 230. An axial fixation projection 234 can be formed to have a generally bulbous of continuous outer surface 236 or to have any appropriate geometry, such as that discussed above. The outer surface of the projection 234 can diverge/converge from the outer surface 232 of the liner 230 at a first divergence point 238 and converge or diverge at a second divergence point 240. A mid-line 242 can be defined as a line that is half way between the first point 238 and the second point 240. The outer surface region 232 can be substantially parallel to a central axis 244 of the liner 230. Thus, the outer surface 232 can define a substantially vertical line. Near an apex of the liner 230 a curved outer surface region 246 can be defined by the liner 230. The axial projection 234, however, can be defined substantially entirely within the cylindrical outer surface region 232.

Accordingly, it is understood that a specific geometry of the axial fixation projection or the liner is not required. For example, the axial projection need not include the specific dimensions illustrated in FIG. 4 and the liner need not be entirely curved. Nevertheless, the axial fixation projection may include dimensions where a majority of the volume of the material of the axial fixation projection is between the mid-line of the axial fixation projection and the apex of the liner 30.

Generally, according to various embodiments, the axial fixation projection 90, 190, 236 initially or is manufactured and provided to include a majority, such as more than 51%, of a material of the axial fixation projection, between the respective midlines and the apex of the liner 30. For example, regarding the axial fixation projection 90 at least 51% of the material that is included in the axial fixation projection 90 is below the midline 140. Thus, the projection 90, 190, 236 according to various embodiments, is asymmetrical about the mid-line 140, 200.

Figure 7A:
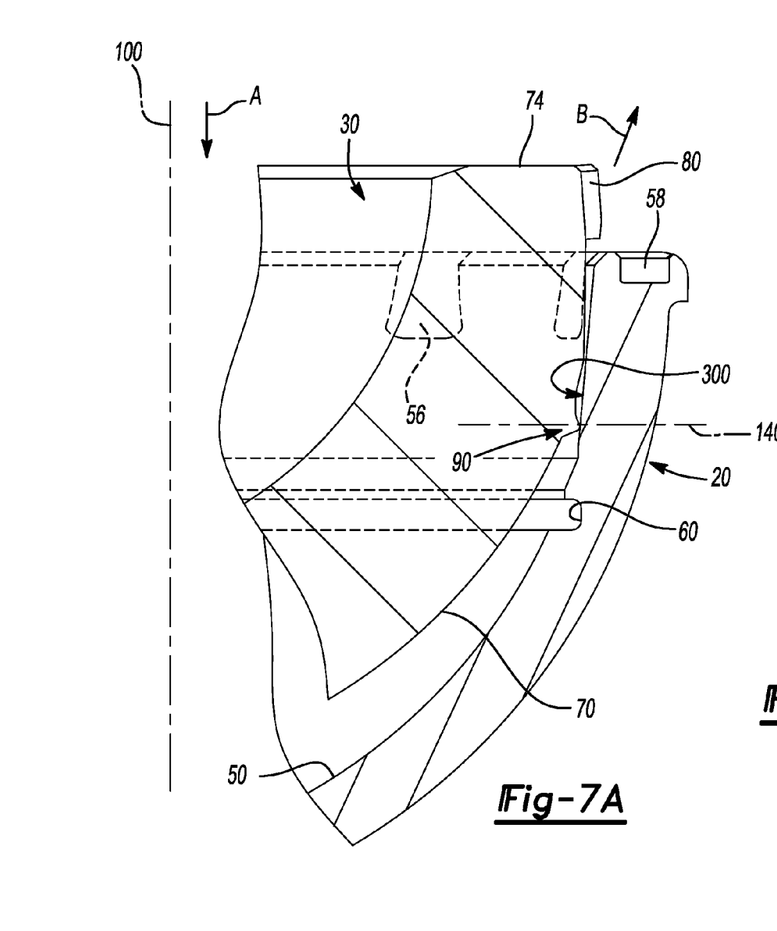
FIG. 7A is a detail cross-section view of the bearing liner being inserted into the shell.
Figure 7B:
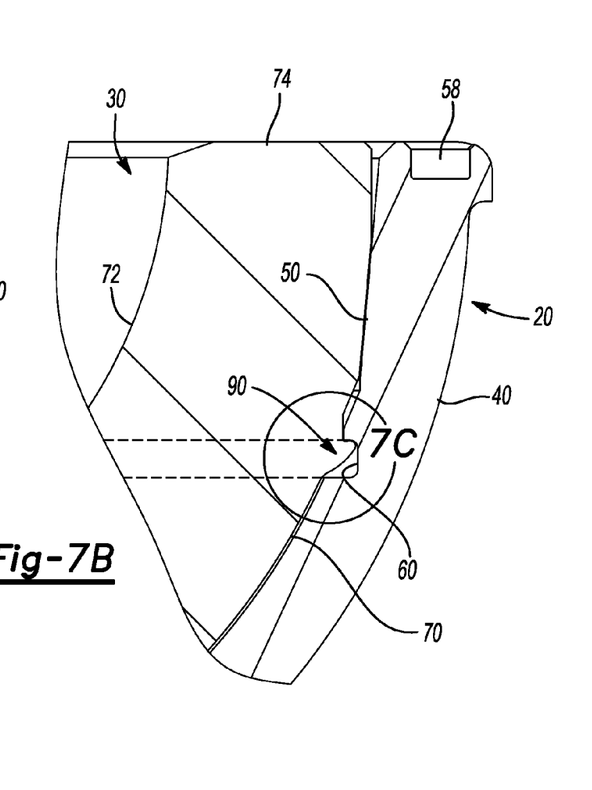
FIG. 7B is a detail cross-section view of the bearing liner seated in the shell.
Figure 7C:
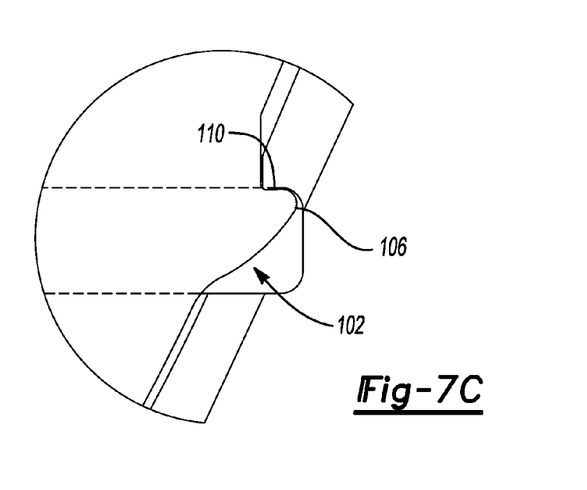
FIG. 7C is a detail cross-section view from FIG. 7B.

With reference to FIGS. 7A-7C, the liner 30 is initially placed relative to the shell 20 in the manufactured configuration where a majority of the material of the axial fixation projection is between the midline and the apex of the liner 30. The liner 30 is then moved into and may be positioned within the shell 20 by applying a substantially axial force in the direction of Arrow A that can generally be along the axis 100 of the liner 30. As the liner 30 is pressed into the shell 20, the axial fixation projection 90 engages the inner wall surface 50 of the shell 20.

As the axial fixation projection 90 engages the inner wall surface 50 of the shell 20, the projection 90 is urged generally in the direction of Arrow B that is substantially in a direction opposite of Arrow A. The projection 90 is generally forced in the direction of Arrow B due to a reaction of pressing the liner 30 into the shell 20. Friction caused between the projection 90 and the inner surface 50 of the shell 20 causes the projection 90 to be urged in the direction of Arrow B. The material of the projection 90 generally does not compress or collapse, but may be mobile under the force of the insertion of the liner 30 into the shell 20. A movement zone can be formed near or at the interface of the projection 90 with the outer surface 70 of the liner 30. The movement zone can include movement of the material from the projection 90 towards the rim 74 of the liner 30. In other words, there is movement of material in the projection 90 from below the mid-line 140 (i.e. an area or volume between the apex 76 and the mid-line 140) to an area above the mid-line 140 (i.e. an area or volume between the rim 74 and the mid-line 140). As the liner 30 is pressed into the shell 20 the friction or engagement between the projection 90 and the inner surface 50 of the shell 20 continues.

As the liner 30 moves into a substantially seated position, as illustrated in FIGS. 7B and 7C, the projection 90 achieves a substantially locking configuration, which can also be viewed a reverse pullout ramp configuration. In the locking configuration, which can be a second and/or deformed configuration, a portion of the material of the projection 90 that was between the mid-line 140 and the apex 76 of the liner 30 has moved between the line 140 and the rim 74 of the liner 30. In the locked configuration, the projection 90, 190, according to various embodiments, may be asymmetrical about the mid-line 140, 200 and biased towards the rim 74 of the liner 30.

In the locked configuration, the material of the projection 90 has been altered or moved to engage the depression or groove 60 of the shell 20 in a locked configuration. The surface of the deformed projection that was initially provided as surface 110 is substantially perpendicular to the central axis of the liner 30 and would engage a surface 60a of the depression prior to other surfaces of the deformed projection. Moreover, the initially provided surface 102 and part or all of surface 106 are angled towards the rim 74 and the central axis 100 of the liner 30.

The movement of the material from the projection 90 from the manufactured configuration (also referred to as the initial configuration) to the locked configuration, as illustrated in FIGS. 7B and 7C, can provide a substantially strong push-out and lever-out force of the liner 30 relative to the shell 20.

The amount of material that moves from the initial position (e.g. as illustrated according to various embodiments in FIGS. 4-6) to the locked position (e.g. as illustrated in FIGS. 7B and 7C) may be selected based upon various considerations and selections. For example, the amount of material that moves can be selected based on materials for the liner 30, the various dimensions of the axial fixation projection 90 (e.g. the first wall 102), the distance from the rim 58 to the recessed depression 60 of the shell 20, and other factors. Generally, according to the various embodiments, projection 90 may include at least 51% of the material of the projection between the mid-line and the apex of the liner and in the locked configuration the projection 90 has at least 51% of the material moved between the mid-line 140 and the rim 74.

Figure 8:
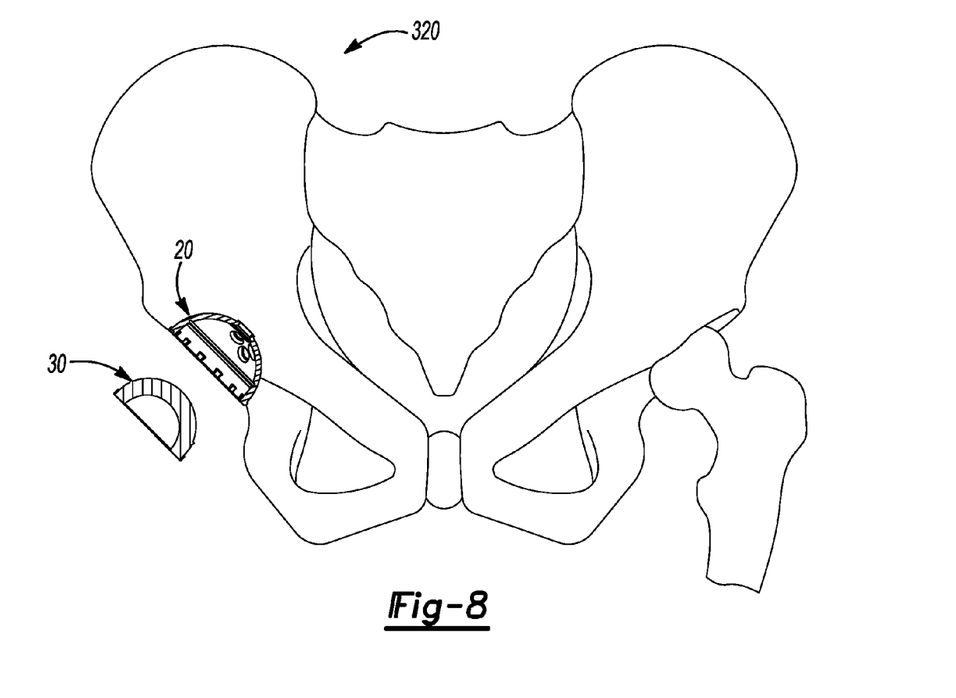
FIG. 8 is an environmental view of the shell and bearing liner relative to a subject.

The liner 30 can be pre-assembled to the shell 20 prior to insertion into a patient. Alternatively, and according to various embodiments, however, the shell 20 can initially be positioned within a patient 320, as illustrated in FIG. 8, and then the liner 30 can be positioned within the shell 20. Assembly of the liner 30 into the shell 20 and positioning the shell 20 into the patient 320 can be performed according to various and commonly known methods, such as that used with the RINGLOC® prosthesis system sold by Biomet, Inc. having a place of business in Warsaw, Ind. Generally, the liner 30 can be pressed into the shell 20 using an insertion tool that can apply enough force to overcome the friction between the projection 90 and the inner surface 50 of the shell 20 and allow the projection 90 to deform for engagement into the groove of the shell 20.

As discussed above, the projection 90 can be formed with the other portions of the liner 30 according to generally known manufacturing techniques. Generally, the liner 30 can be molded using generally known molding and forming techniques. Accordingly, the projection 90 need not be an additional piece that is added to the liner or to the assembly of the shell 20 with the liner 30. The projection 90 being integral with the liner 30 allows for an efficient assembly of the liner 30 with the shell 20. Additionally, additional machining and manufacturing steps for a separate locking mechanism may not be required. Further, the material forming the projection 90 can generally be substantially anatomically and physiologically compatible and additional materials need not be offered to the assembly.

The interaction of the liner 30, including the projection 90, with the inner surface 50 of the shell 20 can provide for a substantially strong lever-out and push-out force. Various standards have been developed in the art to measure forces that act on acetabular prostheses to attempt to disassemble or disconnect the liner 30 from the shell 20. For example, a lever out test, according to the standard ASTM F1820-97 (2009) can measure the amount of force required to lever out the liner 30 from the shell 20. Generally, the liner 30 can be assembled into the shell 20. The shell 20 is then held fixed within an assembly and a leaver arm engages the liner 30 by being pressed into the liner 30 across the diameter of the liner 30. The lever arm is then pressed over a fulcrum to apply a force to attempt to lever out the liner 30 from the shell 20. Generally, the lever out force of the liner 30 including the projection is about 140 foot/pounds (ft/lb) to about 190 ft/lb, including about 160 ft/lb to about 190 ft/lb, and further including about 170 ft/lb to lever out the liner 30 from the shell 20.

Additionally, a push-out force test can also be performed according to the standard ASTM F1820-97 (2009) standard. In a push-out test, the liner 30 is assembled into the shell 20 and the shell 20 is supported by an assembly while the liner 30 is free to move when a force is applied. The force is supplied through the apical hole 42 with a push bar. The push-out force for the liner 30 with the projection 90 assembled within the shell 20 can generally be about 320 ft/lb to about 400 ft/lb, including about 350 ft/lb to about 380 ft/lb, and further including about 370 ft/lb. Accordingly, the assembly of the liner 30 into the shell 20 including only the axial fixation projection 90 can provide a substantial lever-out and push-out forced resistance. Additionally, it is understood, that the other configurations, including that illustrated in FIG. 5, can include similar lever-out and push-out force resistance given the configuration of the axial fixation projection 190 to interact with the shell 20. Generally, the achieved lever-out and push-out forces can be achieved when the projection, according to various embodiment, can achieve the seated or deformed configuration that moves the selected amount of material past a mid-line of the projection. Further, it is understood, that the material of the projection 90 remains in the second or implanted configuration after implantation until acted upon by a member that produces the forces discussed above. That is, the projection 90 does not substantially elastically deform, but maintains the implanted configuration.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for an acetabular prosthesis to fix a bearing liner within a shell, comprising:
   a shell member having an exterior configured to engage an anatomy and a concave interior;
   a bearing liner having an exterior wall surface configured to be received within the concave interior of the shell member, the exterior wall surface extending from a rim of the bearing liner towards an apex of the bearing liner along a substantially continuous curve, and an axial fixation projection extending from the substantially continuous curve of the exterior surface;
   wherein the axial fixation projection has a first projection surface extending from the exterior surface a first distance and at least one second surface extending towards the exterior surface at an acute angle relative to the first projection surface;
   wherein at least 51 percent of the material that forms the axial fixation projection is between a midline of the axial fixation projection and the apex of the bearing;
   wherein the axial fixation projections engages the shell to engage the bearing liner within the concave interior of the shell.

2. The system of claim 1, wherein the first projection surface is substantially perpendicular to a bearing liner axis extending from the apex past the rim.

3. The system of claim 2, wherein the rim defines a bearing plane and the bearing liner axis is substantially perpendicular to the bearing plane and intersects the apex.

4. The system of claim 1, wherein the concave interior is substantially hemispherical.

5. The system of claim 1, wherein the shell defines a groove formed into a wall surface of the concave interior, wherein the axial fixation projection is received within the groove when the bearing liner is seated within the shell.

6. The system of claim 1, further comprising:
   proximal femoral member configured to be implanted into a femur to articulate within the positioned bearing liner.

7. The system of claim 1, wherein the at least one second surface includes a plurality of second surfaces that together extend from an exterior end of the first projection surface to the substantially continuous curve of the exterior surface of the bearing liner.

8. A system for an acetabular prosthesis to fix a bearing liner within a shell, comprising:
   a shell member having an exterior configured to engage an anatomy and a concave interior surface extending from a shell rim to a shell apex, an engagement groove is defined through the concave interior surface;
   a bearing liner having an exterior wall surface configured to be received within the concave interior of the shell member, the exterior wall surface extending from a rim of the bearing liner towards an apex of the bearing liner along a substantially continuous curve, an asymmetrical axial fixation projection extending from the substantially continuous curve of the exterior wall surface;

wherein the asymmetrical axial fixation projection has a first configuration where a volume of material of the asymmetrical axial fixation projection is biased towards the apex of the bearing liner;

wherein the asymmetrical axial fixation projection engages the engagement groove of the shell to engage the bearing liner within the concave interior of the shell in a locking configuration that is deformed from the first configuration due to insertion into the shell and engaging the engagement groove in a second configuration.

9. The system of claim 8, wherein the groove is substantially continuous around the concave interior surface.

10. The system of claim 8, wherein the axial fixation projection is discontinuous around the exterior of the bearing liner.

11. The system of claim 8, wherein the asymmetrical axial fixation projection includes a first projection surface extending from the exterior surface substantially perpendicular to a central axis of the liner and having a surface end a first distance from the exterior surface and positioned a first distance from the rim of the liner;

wherein the asymmetrical axial fixation projection further includes at least one second surface extending towards the central axis at an acute angle relative to the first projection surface and positioned a second distance from the rim, wherein the second distance is less than the first distance.

* * * * *

UNITED STATES PATENT AND TRADEMARK OFFICE
CERTIFICATE OF CORRECTION

| | | |
|---|---|---|
| PATENT NO. | : 8,801,798 B1 | Page 1 of 1 |
| APPLICATION NO. | : 13/763145 | |
| DATED | : August 12, 2014 | |
| INVENTOR(S) | : Aaron P. Smith | |

It is certified that error appears in the above-identified patent and that said Letters Patent is hereby corrected as shown below:

Title Page, item (71), Applicant: Delete "Biomet Manufacturing Corporation" and insert --Biomet Manufacturing, LLC--.

Signed and Sealed this
Twenty-sixth Day of May, 2015

Michelle K. Lee
*Director of the United States Patent and Trademark Office*